United States Patent [19]
Parker et al.

[11] Patent Number: 5,614,507
[45] Date of Patent: Mar. 25, 1997

[54] PROTEIN AND PEPTIDE FREE, NEUTRAL LIPID AND PHOSPHOLIPID CONTAINING COMPOSITIONS USEFUL IN TREATING ENDOTOXEMIA

[75] Inventors: Thomas S. Parker, Brooklyn; Daniel M. Levine, New York, both of N.Y.; Albert L. Rubin, Englewood, N.J.; Bruce R. Gordon; Stuart D. Saal, both of New York, N.Y.

[73] Assignee: The Rogosin Institute, New York, N.Y.

[21] Appl. No.: 432,691

[22] Filed: May 2, 1995

Related U.S. Application Data

[60] Division of Ser. No. 288,568, filed as PCT/US93/07453, Aug. 9, 1993, Pat. No. 5,506,218, which is a continuation-in-part of Ser. No. 928,930, Aug. 12, 1992, Pat. No. 5,344,822.

[51] Int. Cl.$^6$ .................... A61K 31/685; A61K 31/56; A61K 31/225
[52] U.S. Cl. ................. 514/78; 514/182; 514/547
[58] Field of Search .................. 514/78, 182, 547

[56] References Cited

U.S. PATENT DOCUMENTS 4,703,062 10/1987 Blackburn et al. .................... 514/552
5,000,958 3/1991 Fountain et al. ....................... 424/450

FOREIGN PATENT DOCUMENTS 0071995 2/1983 European Pat. Off. .

OTHER PUBLICATIONS

CA 114:2291, Morton et al., 1990.
Cuéet al., "Recognized High Density Lipoprotein Inhibits Physiologic and Tumor Necrosis Factor α Responses to Lipopolysaccharide in Rabbits", Arch. Surg. 129: 197 (Feb. 1994).
Glueck et al., "severe hypertriglyceridemia and pancreatitis when estrogen replacement therapy is given to hypertriglyceridemic women", J. Lab. Clin. Med. 123: 59–Γ(1994).
Read et al., "Chylomicrons Enhancer Endotoxin Excretion in Bile", Infect & Immun. 61(8): 3496–3502 (Aug. 1993).
Harris et al., "Chylmicrons Alter The Fate of Endotoxin Decreasing Tumor Necrosis Factor Release and Preventing Death", J. Clin. Invest. 91: 1028–1034 (Mar. 1993).
Eichbaum et al., "Chylomicrons Can Inhibit Endotoxin Activity In Vitro", J. Surg. Res. 51(5): 413–416 (Nov. 1991).
Feingold et al., "Endotoxin Rapidly Induces Changes In Lipid Metabolism that Produce Hypertriglyceridemia: Low Doses Stimulated Hepatic Triglyceride Production While High doses Inhibit Clearance:," J. Lipid Res. 33: 1765–1776 (1992).
Harris et al., "Detection of Endotoxin In Triglyceride Rich Liproproteins In Vitro", J. Lab. Clin. Med. 118: 186–193 (1991).
Harris et al., "Human Very Low Density Lipoproteins and Chylomicrons Can Protect Against Endotoxin Induced Death In Mice", J. Clin. Invest. 86: 696–702 (Sep. 1990).
Farmer et al., "Hyper lipoproteinemia and Pancreatitis", Am. J. Med. 54: 161–165 (1973).
Maranhao et al., "Metabolic Behavior in Rats of a Nonprotein Microemulsion Resembling Low Density Lipoprotein", Lipids 28(8): 691–695 (1993).
Miller and Small, "Structure of Triglyceride–Rich Lipoproteins: Analysis of Care & Surface Phases" in gotto, Jr.; ed. Plasma Lipoproteins (Elsevier Science Publishers 1987), pp. 1–69.

Primary Examiner—Kimberly Jordan
Attorney, Agent, or Firm—Felfe & Lynch

[57] ABSTRACT

Protein and peptide free compositions are described, which are useful in treating endotoxemia. The compositions contain a phospholipid and a neutral lipid, preferably phosphatidylcholine and triglyceride.

9 Claims, 15 Drawing Sheets

Polar Face
18A

Polar Face
Reverse 18A des Val¹⁰ 18A

Polar Face
AP

LAP-16

LAP-20

LAP-24

APOA-I CONSENSUS

Polar Face
APOA-IV CONSENSUS

PROTEIN AND PEPTIDE FREE, NEUTRAL LIPID AND PHOSPHOLIPID CONTAINING COMPOSITIONS USEFUL IN TREATING ENDOTOXEMIA

This application is a divisional of Ser. No. 08/288,568, filed Aug. 10, 1994, now U.S. Pat. No. 5,506,218, which is a continuation-in-part of PCT application PCT/US 93/07453 filed Aug. 9, 1993, which is a continuation-in-part of U.S. patent application Ser. No. 07/928,930, filed Aug. 12, 1992, now U.S. Pat. No. 5,344,822.

FIELD OF THE INVENTION

This invention relates to the treatment of endotoxin related endotoxemia. More particularly, it relates to the treatment of such poisoning via administration of various compositions which act to neutralize and/or to remove endotoxins from the organism, as well as prophylaxis utilizing these compositions.

BACKGROUND AND PRIOR ART

Normal serum contains a number of lipoprotein particles which are characterized according to their density, namely, chylomicrons, VLDLs, LDLs and HDLs. They are composed of free and esterified cholesterol, triglycerides, phospholipids, several other minor lipid components, and protein. Very low density lipoprotein (VLDL) transports energy, in the form of triglycerides, to the cells of the body for storage and use. As triglycerides are delivered, VLDL is converted to low density lipoprotein (LDL). Low density lipoprotein (LDL) transports cholesterol and other lipid soluble materials to the cells in the body, while high density lipoprotein (HDL) transports excess or unusable cholesterol to the liver for elimination. Normally, these lipoproteins are in balance, ensuring proper delivery and removal of lipid soluble materials. Abnormally low HDL can cause a number of diseased states as well as constitute a secondary complication in others.

Under normal conditions, a natural HDL is a solid particle with its surface covered by a phospholipid monolayer that encloses a hydrophobic core. Apolipoprotein A-I and A-II attach to the surface by interaction of the hydrophobic face of their alpha helical domains. In its nascent or newly secreted form the particle is disk-shaped and accepts free cholesterol into its bilayer. Cholesterol is esterified by the action of lecithin:cholesterol acyltransferase (LCAT) and is moved into the center of the disk. The movement of cholesterol ester to the center is the result of space and solubility limitations within the bilayer. The HDL particle "inflates" to a spheroidal particle as more and more cholesterol is esterified and moved to the center. Cholesterol ester and other water insoluble lipids which collect in the "inflated core" of the HDL are then cleared by the liver.

Anantharamaiah, in Segrest et al., Meth. Enzymol. 128: 627–647 (1986) describes a series of peptides which form "helical wheels", as a result of the interaction of the amino acids in the peptide with each other. Such helical wheels present a nonpolar face, and a polar face in their configuration. The reference shows, generally, that peptides can replace aproproteins in these particles.

Jonas et al., Meth. Enzym. 128A: 553–582 (1986) have produced a wide variety of reconstituted particles resembling HDL. The technique involves the isolation and delipidation of HDL by standard methods (Hatch et al., Adv. Lip. Res. 6: 1–68 (1968); Scanu et al., Anal. Biochem. 44: 576–588 (1971) to obtain apo-HDL proteins. The apoproteins are fractionated and reconstituted with phospholipid and with or without cholesterol using detergent dialysis.

Matz et al., J. Biol. Chem. 257(8): 4535–4540 (1982) describe a micelle of phosphatidylcholine, with apolipoprotein A1. Various ratios of the two components are described, and it is suggested that the described method can be used to make other micelles. It is suggested as well to use the micelles as an enzyme substrate, or as a model for the HDL molecule. This paper does not, however discuss application of the micelles to cholesterol removal, nor does it give any suggestions as to diagnostic or therapeutic use.

Williams et al., Biochem. & Biophys. Acta 875: 183–194 (1986) teach phospholipid liposomes introduced to plasma which pick up apoproteins and cholesterol. Liposomes are disclosed, which pick up apoprotein in vivo, as well as cholesterol, and it is suggested that the uptake of cholesterol is enhanced in phospholipid liposomes which have interacted with, and picked up apoproteins.

Williams et al., Persp. Biol. & Med. 27(3): 417–431 (1984) discuss lecithin liposomes as removing cholesterol. The paper summarizes earlier work showing that liposomes which contain apoproteins remove cholesterol from cells in vitro more effectively than liposomes which do not contain it. They do not discuss in vivo use of apoprotein containing liposomes or micelles, and counsel caution in any in vivo work with liposomes.

It is important to note that there is a clear and significant difference between the particles of the present invention, and the liposomes and micelles described in the prior art. The latter involve a bilayer structure of lipid-containing molecules, surrounding an internal aqueous core space. The structure of liposomes precludes filling the internal space with a lipid soluble component, however, and any molecular uptake of lipid soluble components is limited to the space defined between the two lipid layers. As a result, there is much less volume available for pick up and discharge of materials such as cholesterol and other lipid soluble materials than there is for the particles of this invention, which expand in a fashion similar to a balloon, with interior space filling with the material of choice.

Endotoxic shock is a condition, often fatal, provoked by the release of lipopolysaccharide (LPS) from the outer membrane of most gram negative bacteria (e.g., *Escherichia coli; Salmonella tymphimurium*). The structure of the bacterial LPS has been fairly well elucidated, and a unique molecule, referred to as lipid A, which is linked to acyl chains via lipid A molecule's glucosamine backbone is a component of LPS. See Raetz, Ann. Rev. Biochem. 59: 129–170 (1990) in this regard.

The lipid A molecule serves as membrane anchor of a lipopolysaccharide structure ("LPS") and it is the LPS which is implicated in the development of endotoxic shock. It should be pointed out that LPS molecules are characterized by a lipid A type structure and a polysaccharide portion. This latter moiety may vary in molecular details in different LPS molecules, but it will retain the general structural motifs characteristic of endotoxins. It would be incorrect to say that the LPS molecule is the same from bacteria to bacteria (see Raetz, supra). It is common in the art to refer to the various LPS molecules as "endotoxins", and this term will be used hereafter to refer to LPS molecules collectively.

In U.S. Pat. No. 5,128,318 the disclosure of which is incorporated by reference, it was taught that reconstituted particles containing both an HDL associated apolipoprotein and a lipid capable of binding an endotoxin to inactivate it could be used as effective materials for alleviating endotoxin caused toxicity.

In the parent and grandparent applications cited in the Related Application section and incorporated by reference herein, it was disclosed that various other materials may be used to treat endotoxin caused toxicity. Specifically, it was found that apolipoproteins are not required in reconstituted particles, and that the reconstituted particle may contain a peptide and a lipid wherein the peptide is not an apolipoprotein.

It was also found by the inventors that endotoxin caused toxicity may be treated via sequential administration of either an apolipoprotein or a peptide followed by a lipid. Following sequential administration, the components assemble as a reconstituted particle and then act to remove endotoxin.

It was also found that at least some individuals possess native levels of apoliprotein which are higher than normal levels such that effective endotoxemia therapy may be effectuated by administering reconstituted particles containing no apolipoprotein or peptide, but containing the lipid of the disclosure.

In addition, the invention disclosed in these applications involved the use of the reconstituted particles and the components discussed herein for prophylaxis against endotoxin caused toxicity, by administering prophylactically effective amounts to subjects in need of prophylaxis. Such subjects include patients suffering from infections or recovering from surgery. These patients sometimes have very low plasma HDL levels, sometimes as little as 20% of normal levels. It is highly desirable, in these cases, for early prophylaxis with HDL, so as to compensate for these drops.

It has now been found, quite surprisingly, that phospholipids may be used alone, or in combination with neutral lipids, as effective agents to alleviate and/or prevent endotoxemia. It is especially preferred to use phosphatidylcholines ("PC" hereafter), either alone, or in combination with other phospholipids, such as sphingolipids, in compositions which are essentially free of peptides and proteins, such as apolipoproteins or peptides derived therefrom. Neutral lipids such as mono-, di-, and triglycerides may be combined with the phospholipids, as long as the total amount of neutral lipids is below certain weight percents when the compositions are used in the form of an intravenous bolus. When used in other forms of administration, such as intravenously for example, by continuous infusion, the weight percents are not so critical, but are desirable.

Particularly preferred embodiments of the invention are those compositions where the neutral lipid is cholesterol ester, or a mixture of cholesterol ester and triglycerides.

The invention is described in greater detail in the disclosure which follows.

DESCRIPTION OF THE FIGURES

FIG. 5A shows the role of protein, and 5B that of phospholipid. The compositions tested included natural lipoproteins (VLDL, LDL, HDL), reconstituted HDL ("R-HDL"), and INTRALIPID® compositions, as well as emulsions containing phospholipid and protein.

DETAILED DESCRIPTION OF THE EMBODIMENTS

EXAMPLE 1

Studies were carried out to determine the survival rate of mice challenged with S. tymphimurium endotoxin. Outbred male, Swiss-Webster mice received either saline solution (20 mice), reconstituted HDL particles (40 mice), or reconstituted peptide 18A (20 mice), via injection through the tail vein. The particulars of the injection materials are as follows:

a. HDL particles

Particles were prepared from apo-Hu-HDL (85%-AI; 15% AII and apo C), reconstituted with 95% pure egg phosphatidylcholine (2:1 W/W), using detergent dialysis, in accordance with Matz et al., J. Biol. Chem. 257: 4535–4540 (1982), and U.S. Pat. No. 5,128,318, the disclosure of which is incorporated by reference.

b. peptide particles

The peptide 18A has the amino acids sequence: Asp-Trp-Leu-Lys-Ala-Phe-Tyr-Asp-Lys-Val-Ala-Gly-Lys-Leu-Lys-Glu-Ala-Phe (SEQ ID NO:1)

Samples of peptide were also mixed and reconstituted with 95% pure eggs phosphatidylcholine as per Matz et al., supra (2:1 w/w), and U.S. Pat. No. 5,128,318 also using detergent dialysis. The resulting particles are identical to those disclosed in U.S. Pat. No. 5,128,318 except that a peptide component was present, rather than the apo-HDL of the Matz and patent references.

Figure 1:
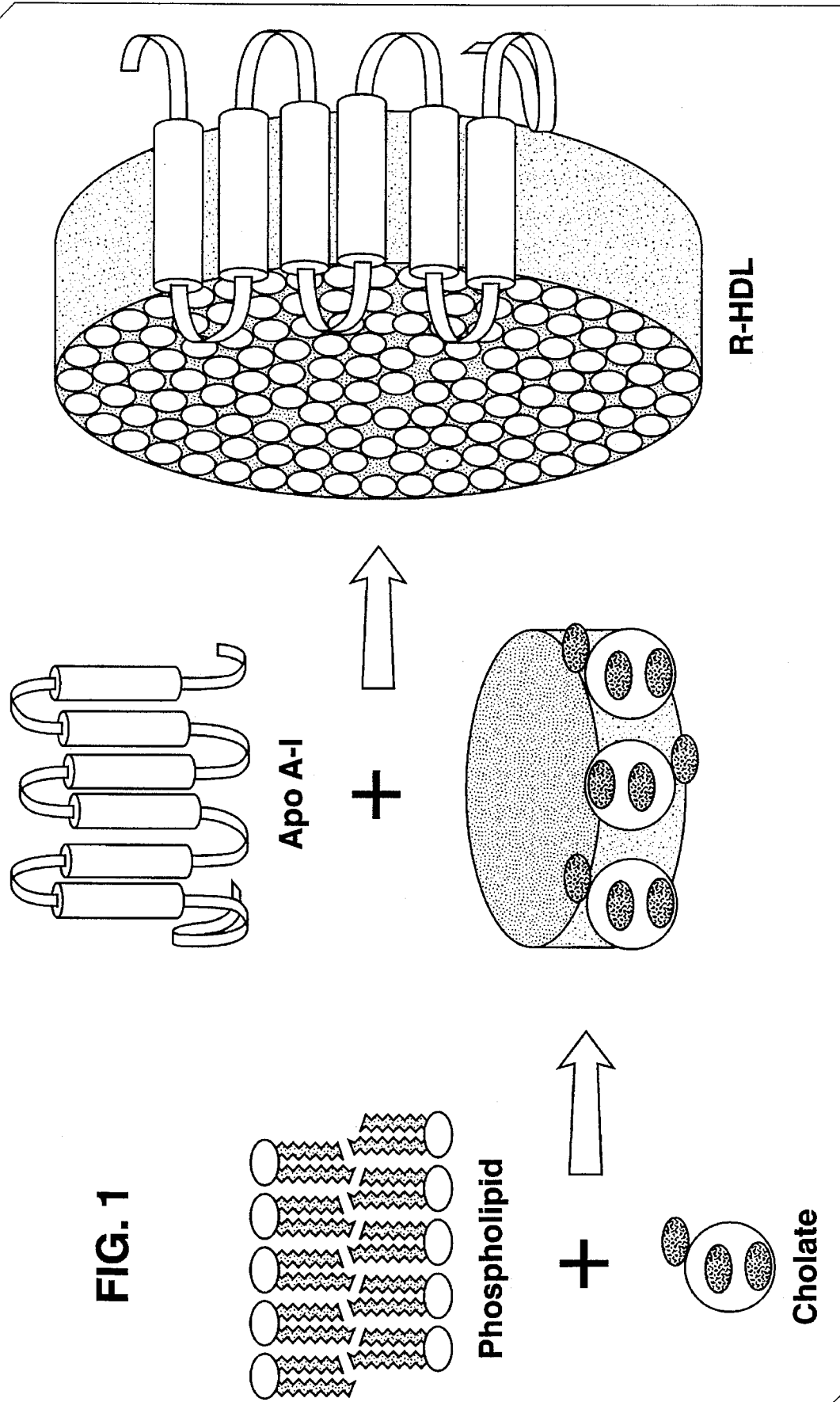
FIG. 1 shows how reconstituted particles containing Apo-A1, phospholipid and cholate form.
Figure 2:
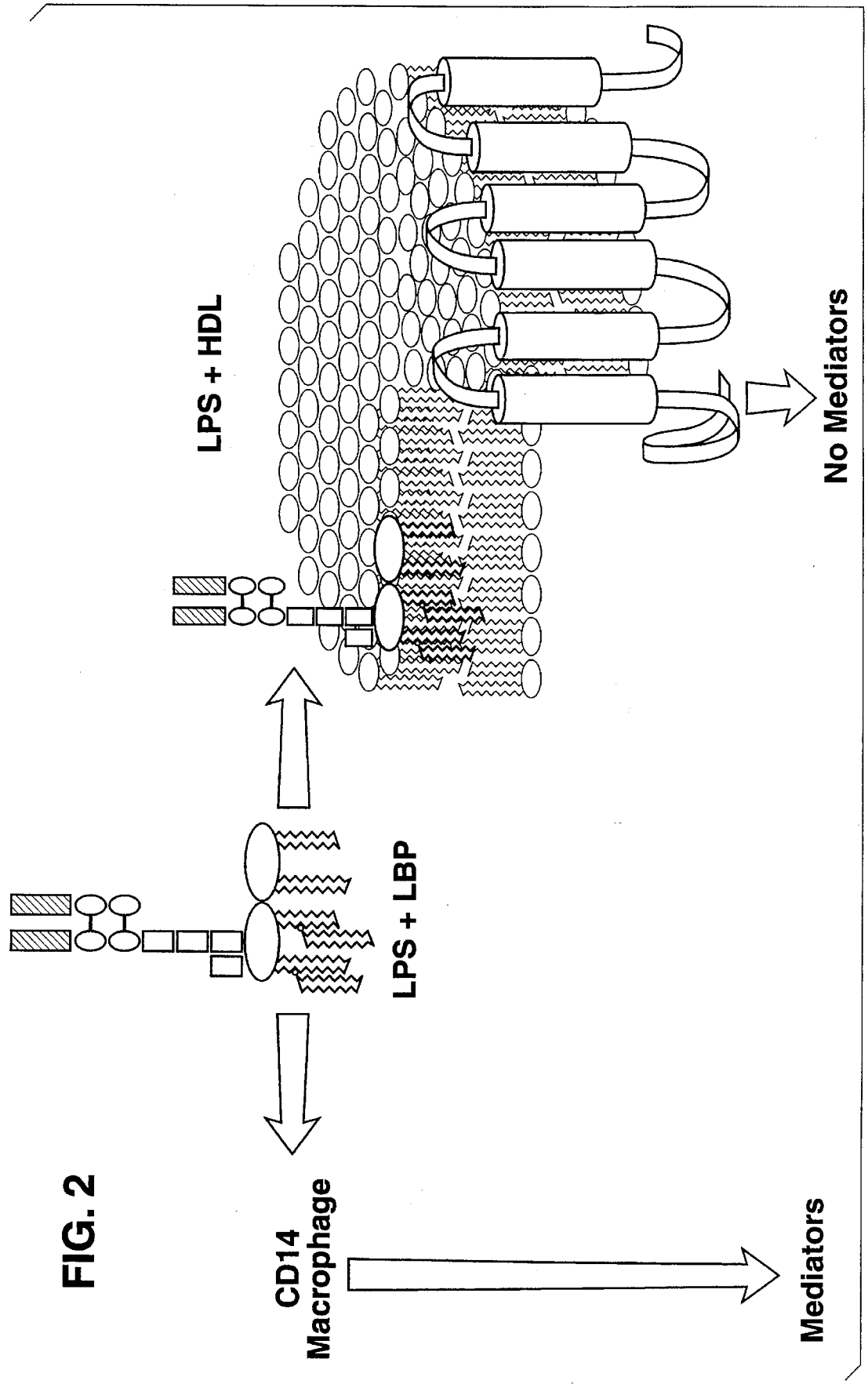
FIG. 2 shows the reception of LPS molecules by reconstituted particles.
Figure 3:
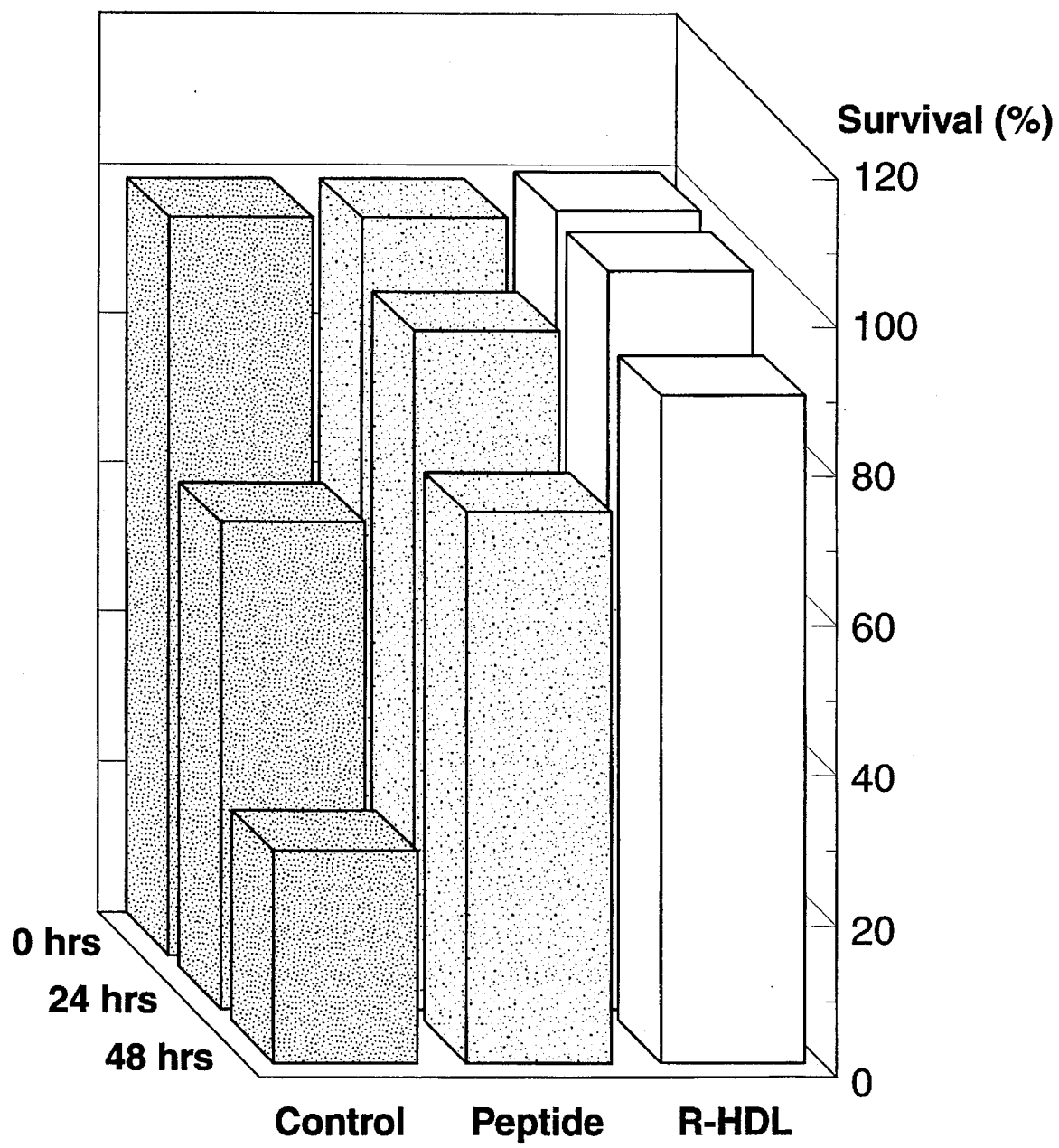
FIG. 3 shows experiments in which a peptide in accordance with the invention as used to study reduction of endotoxin caused toxicity in a mouse model.
Figure 4A:
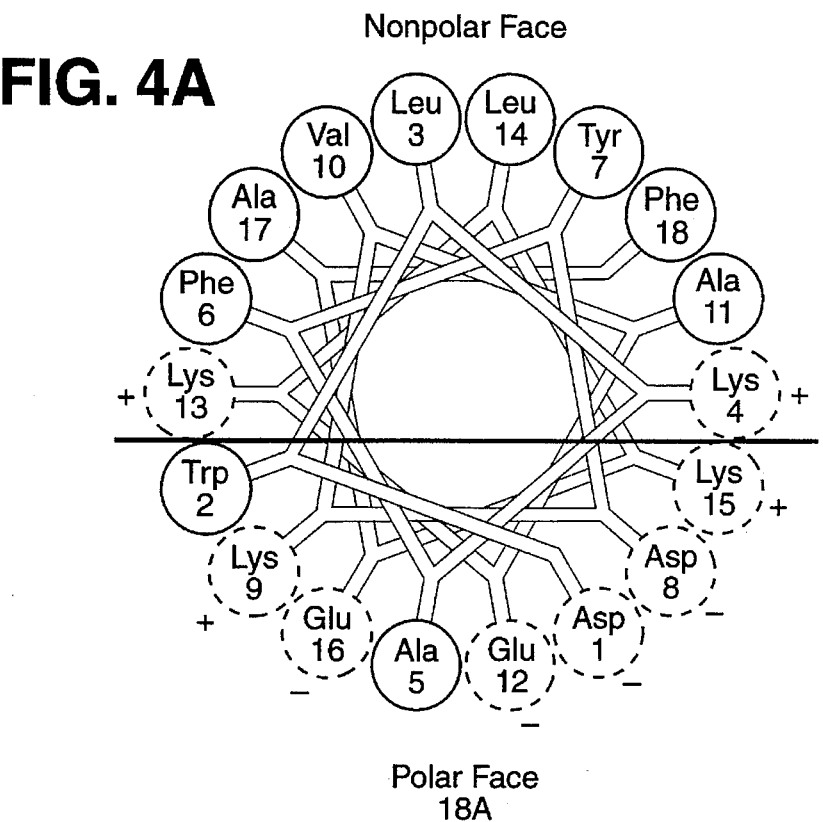
FIG. 4, labelled prior art, shows the formation of helical wheels by various peptides. See Anantharamaiah, supra.
Figure 4B:
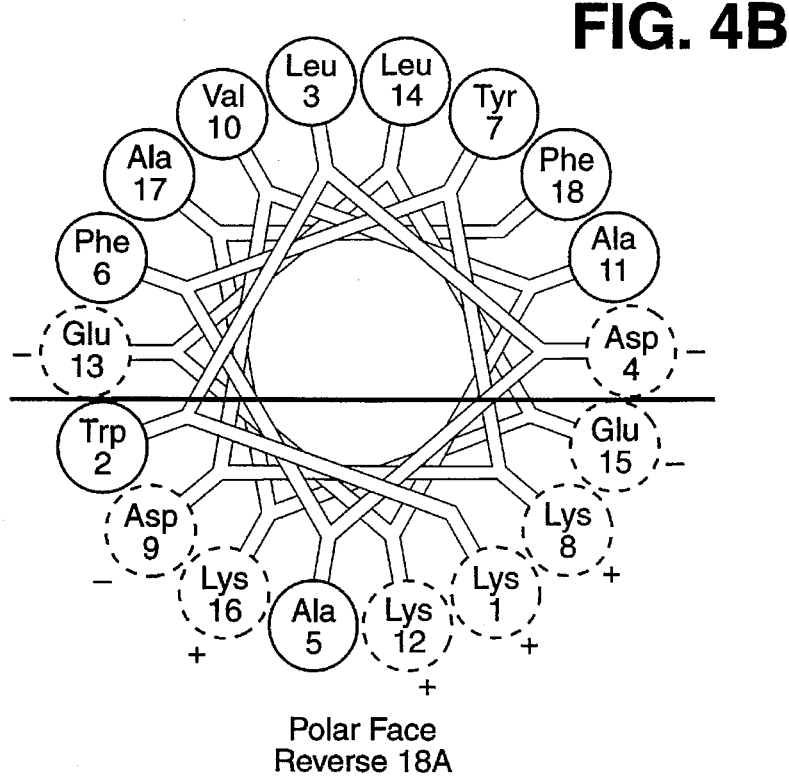
Figure 4C:
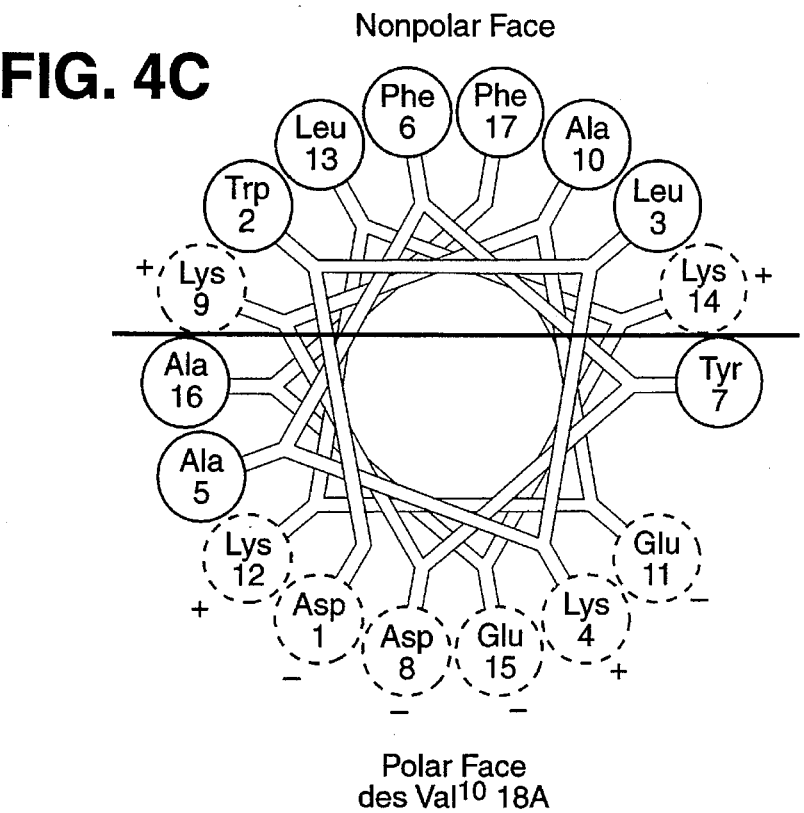
Figure 4D:
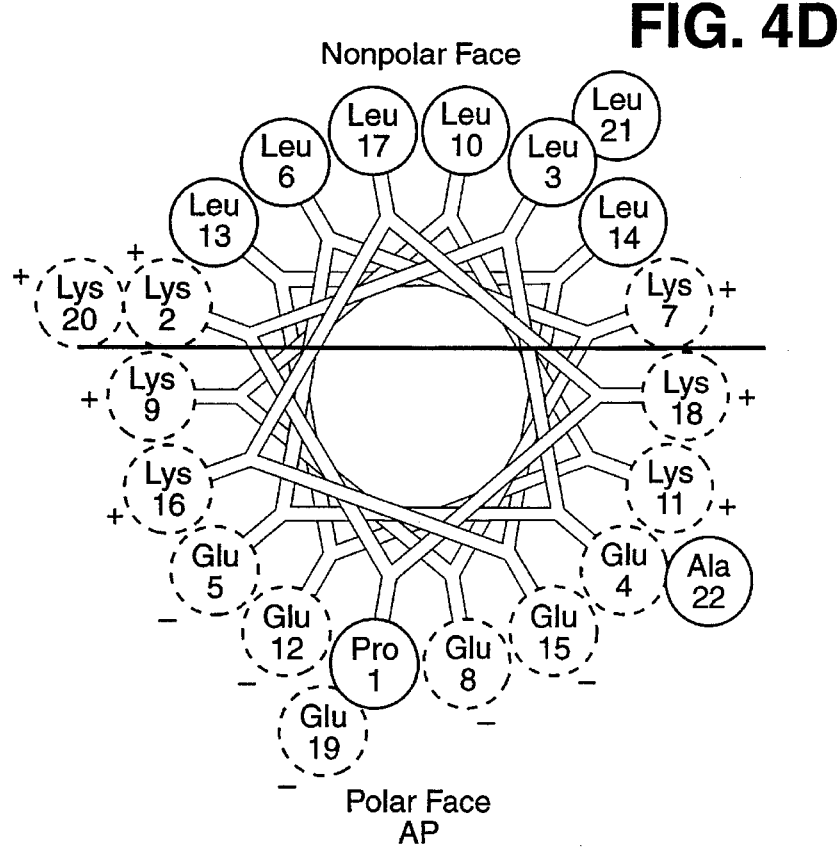
Figure 4E:
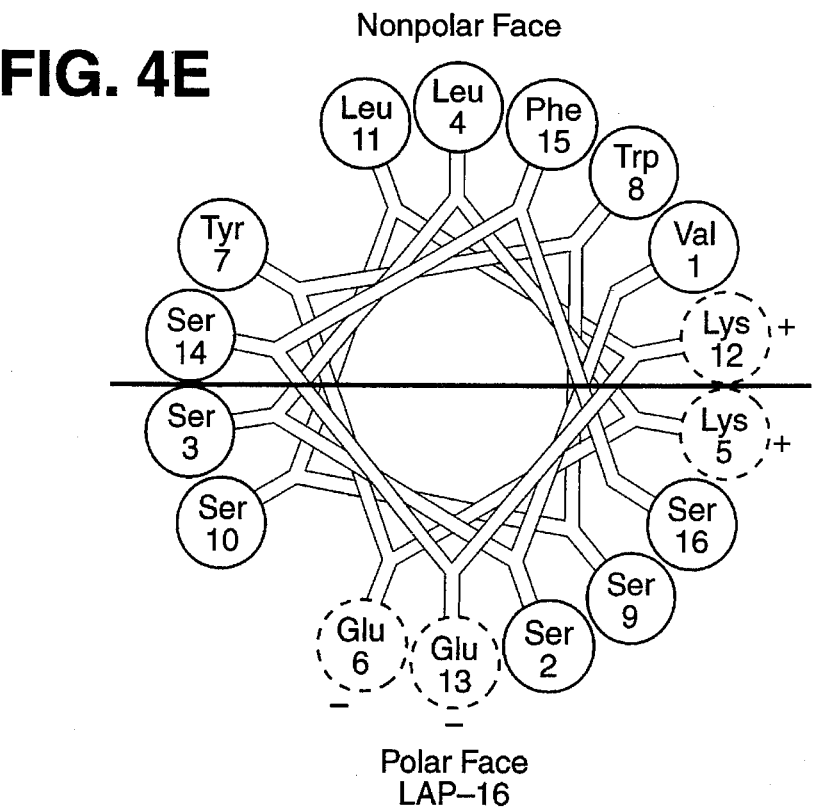
Figure 4F:
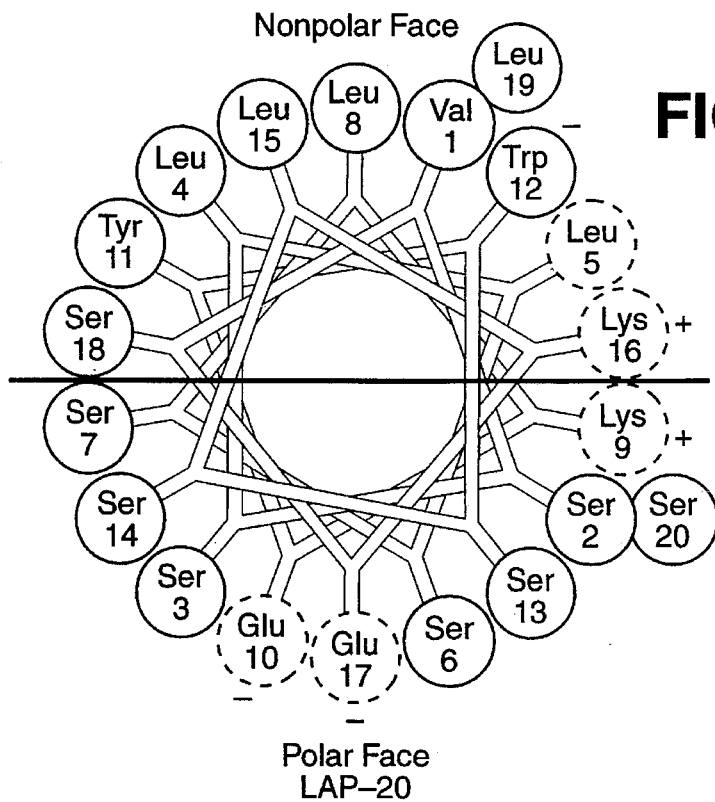
Figure 4G:
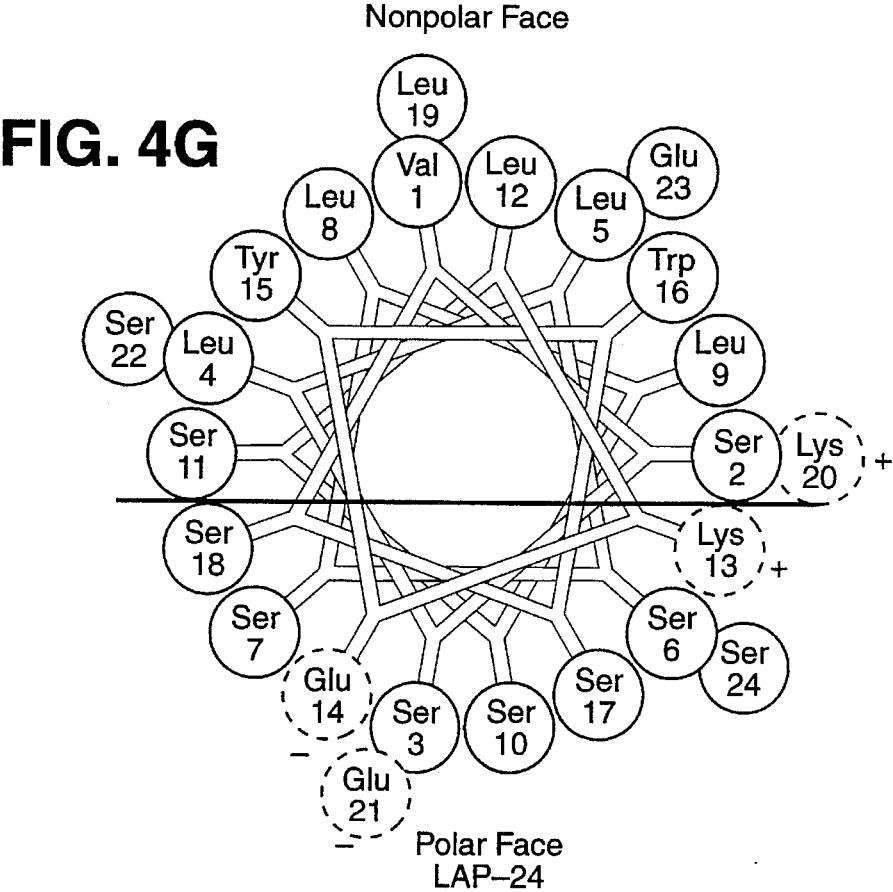
Figure 4H:
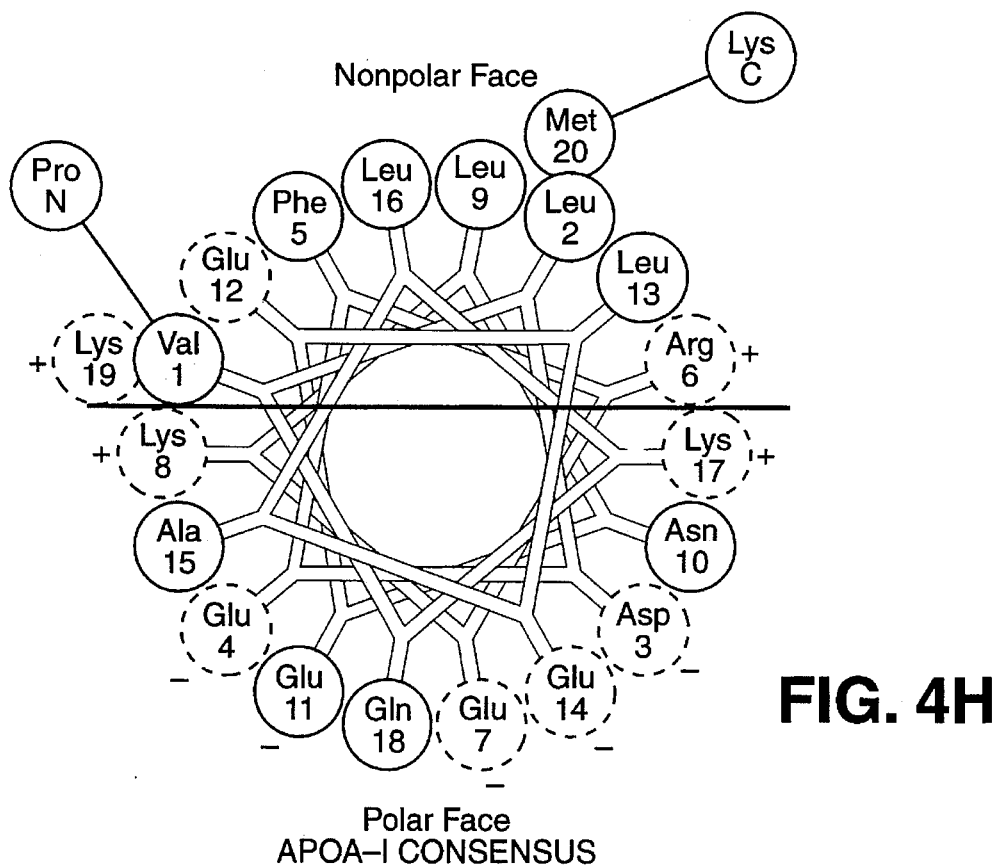
Figure 4I:
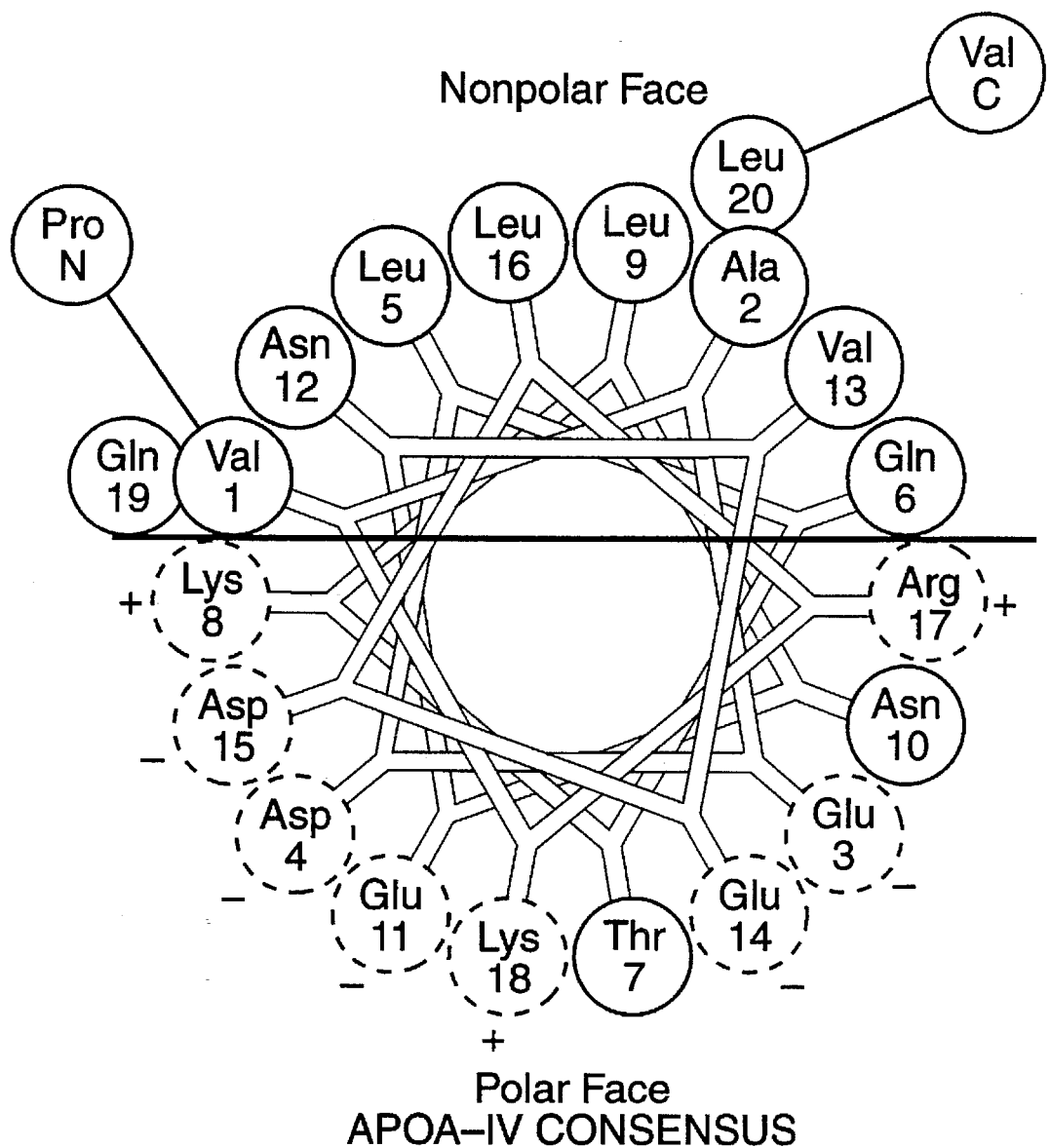

Within fifteen minutes of administration of the reconstituted material, the mice were administered, intraperitoneally, 10 mg/kg body weight of Salmonella LPS. The criterion for evaluation was survival. FIG. 3 presents these results, and indicates nearly 4 fold superiority over the saline control. The synthetic peptide is almost as effective as the reconstituted apo-HDL containing particles.

EXAMPLE 2

Factors which affect the LPS-mediated stimulation of TNF-α while preserving the integrity of interaction between plasma proteins, and cellular elements of blood, can be appropriately studied in an in vitro, human whole blood system. Such a system was used to determine which of the components of lipoproteins is important in neutralizing LPS.

Materials tested were reconstituted high density lipoprotein (R-HDL), natural plasma lipoproteins (VLDL, LDL, HDL), lipoprotein deficient serum (LPDS), and the triglyceride rich emulsion 20% INTRALIPID® (a mixture of triglycerides and phospholipids).

All particles described herein were made via the same protocol, which involved mixing a phospholipid, sphingomyelin or phosphatidylcholine, triolein, and/or unesterified cholesterol ester, dissolved in chloroform, and weighing it into a flask. Vitamin E (0.02% w/v) was added as antioxidant. A dry lipid film was then prepared by blowing nitrogen or argon gas over the sample. A volume of non pyrogenic saline was then added to the flask, followed by mixing on a vortex mixer until all lipid was suspended. The solution was then homogenized in a high pressure homogenizer. Samples containing phosphatidylcholine (PC), with or without triolein, were cycled through the homogenizer 10 times at 20,000 psi. Samples containing cholesterol ester with one or more other lipids were cycled through 15–20 times at 30,000 psi. Homogenized solutions were filtered through 0.45 μm syringe filters, and the filtrate was stored at room temperature until used (within three days).

Blood was collected in a heparinized tube, diluted with Hank's Balanced Salt Solution ("HBSS" hereafter), or the material to be tested, dissolved in HBSS. The resulting material was transferred to Starstedt tubes (250 ul/tube). LPS was dissolved in pyrogen free saline containing 10 mM HEPES, and added (2.5 ul) to a final concentration of 10 ng/ml. After incubation for four hours at 37° C., tubes were chilled to 4° C., followed by centrifugation at 10,000 xg for 5 minutes. Supernatant was collected, and assayed for determination of TNF-α, using a commercially available ELISA.

Figure 5A:
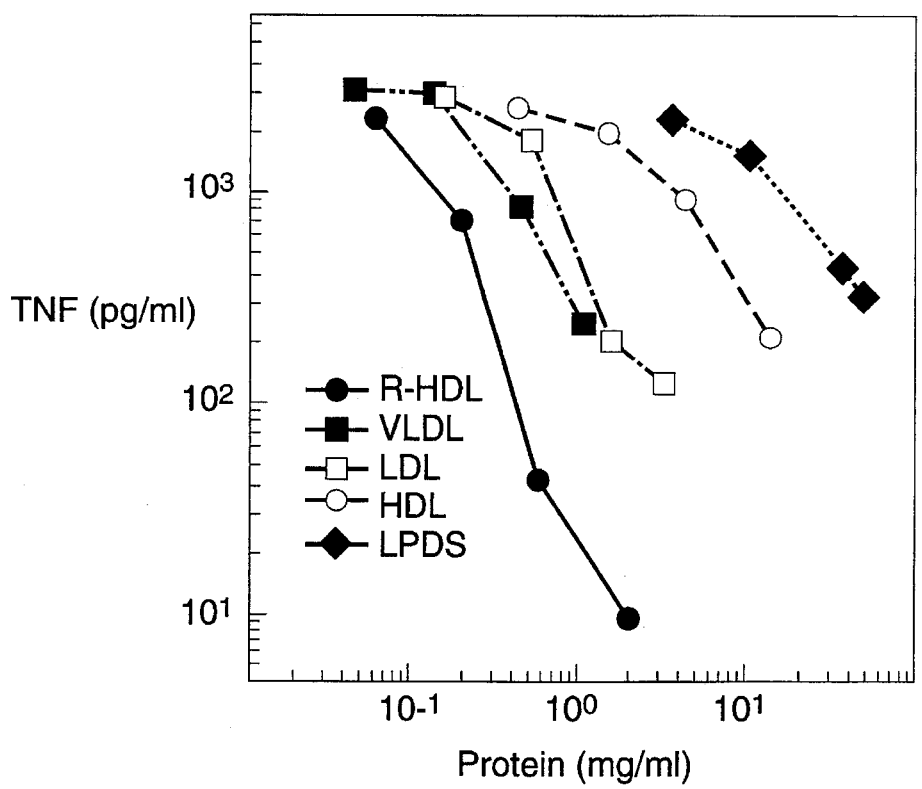
FIGS. 5A and 5B show results obtained when various compositions were tested in a model which determined the neutralization of endotoxin via determining TNF release in a human whole blood model.
Figure 5B:
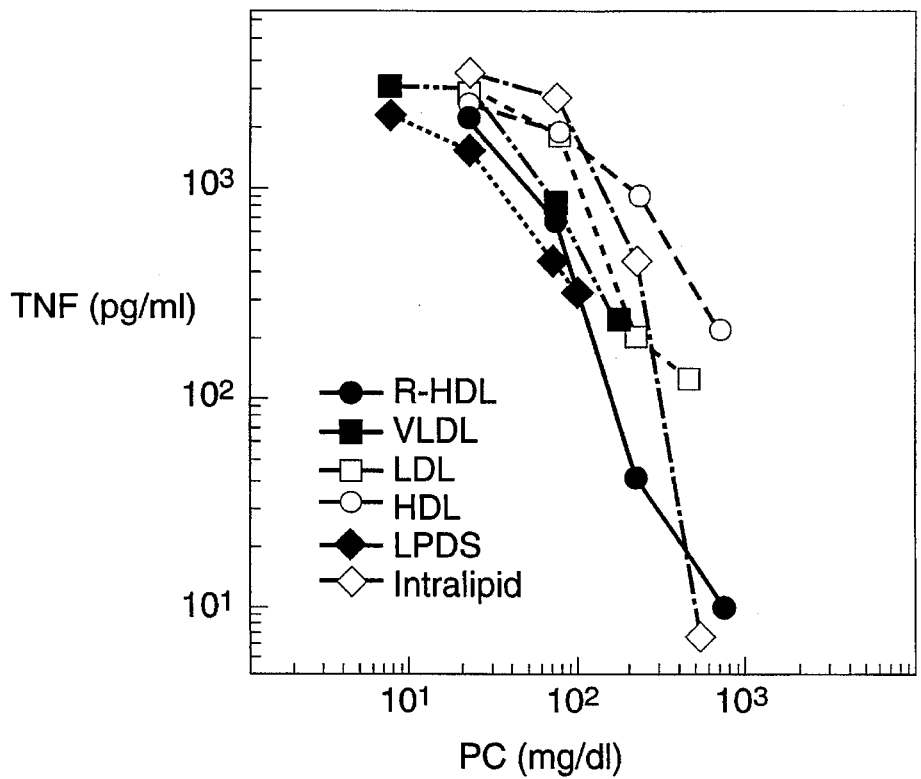

Table 1, which follows, compares the compositions of the materials tested. FIGS. 5A and 5B present the results. Data are plotted as amount of TNF-α produced, plotted against concentration of added protein (FIG. 5A), and phospholipid (FIG. 5B). Logarithmic scales were used, in order to display the wide range of concentrations used, with 10° equal to 1 mg/ml. All whole blood incubations contained 10 ng/ml of E. coli 0111:B4 LPS, supplemented with one of the compositions, as the key for FIGS. 5A and 5B show.

The fact that the materials differ in effectiveness when protein content is plotted (FIG. 5A), while being very similar when phospholipid content is plotted (FIG. 5B) suggest that the phospholipid is the important component. This is confirmed by the finding that a protein free lipid emulsion is more effective than is natural HDL, but less effective than R-HDL. Protein does not appear important to the neutralization.

| Composition of natural lipoproteins and reconstituted HDL | | | | | |
|---|---|---|---|---|---|
| Lipoprotein | | TC | TG | PC | Protein |
| Class | Density (g//ml) | Weight % | | | |
| VLDL | <1.006 | 22 | 53 | 18 | 7 |
| LDL | 1.007–1.063 | 48 | 11 | 22 | 20.9 |
| HDL | 1.063–1.21 | 18 | 8 | 22 | 52 |
| R-HDL | 1.063–1.21 | — | — | 79 | 21 |
| LPDS | >1.21 | 0 | 0 | 2 | 98 |
| Intralipid | — | | 1 | 93 | 6 | 0 |

EXAMPLE 3

Figure 6A:
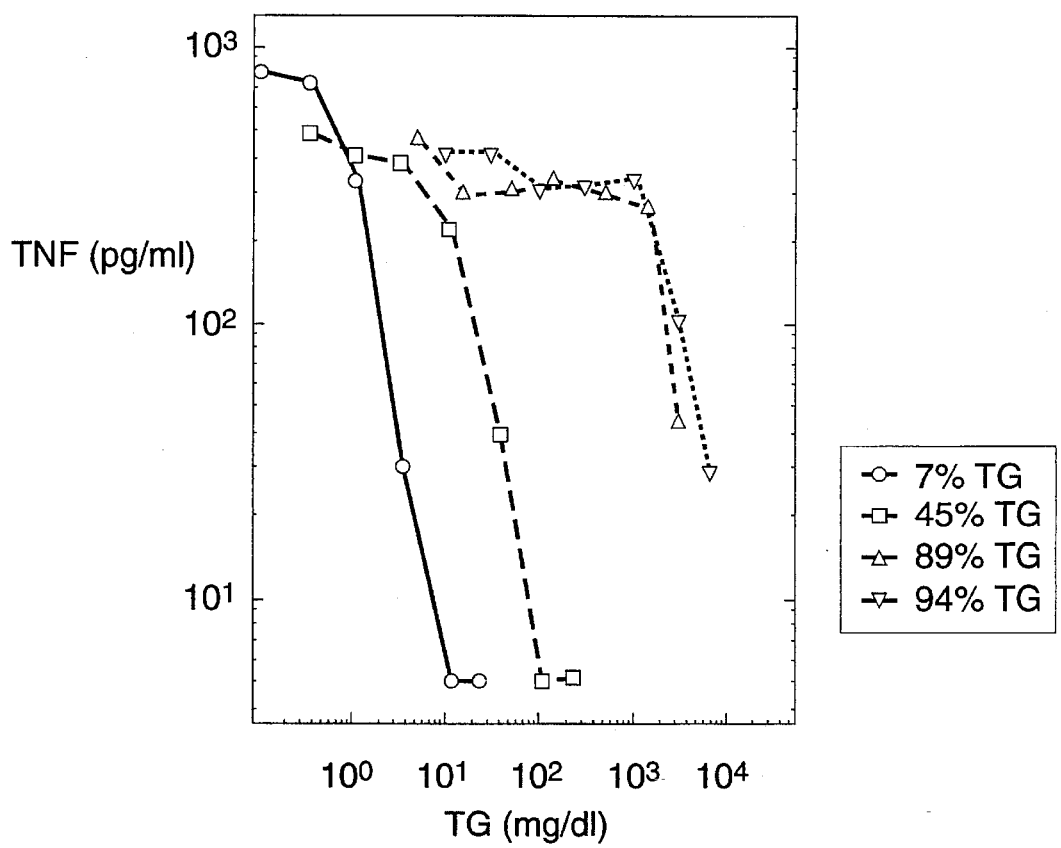
FIGS. 6A and 6B compare the role of triglyceride (a neutral lipid), and phosphatidylcholine, a phospholipid, in the same model.
Figure 6B:
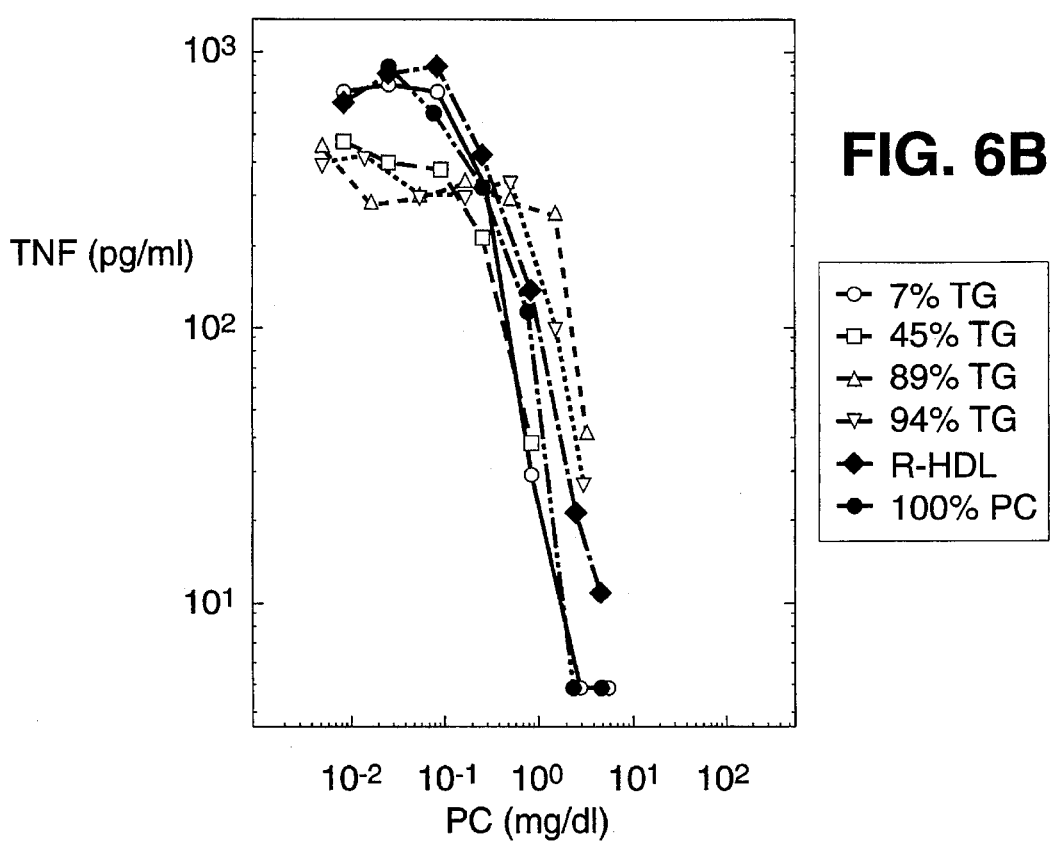

As the next step, protein free lipid emulsions, containing different amounts of neutral lipid, were tested in human whole blood. The same in vitro human whole blood assay as set forth in example 2 was used. FIGS. 6A and 6B present these results. In these studies, LPS-dependent, TNF-α production is plotted against concentration of added triglyceride (FIG. 6A), or phospholipid (FIG. 6B). The compositions, as indicated by the key, contained (by weight) 7% triglyceride ("TG"), 45% TG, 89% TG, 94% TG, R-HDL, or phospholipid without TG, (shown in FIG. 6B only). An 89% TG composition is a 10% INTRALIPID® formulation, while 94% TG refers to 20% INTRALIPID. In all other tests, egg phosphatidylcholine (PC), and triolein were used.

These results show that the protein free compositions, when compared via triglyceride content, are very different. They are very similar when tested via phospholipid (PC) content. This confirms the role of phospholipid, especially since phospholipid alone is effective, but less so than emulsions containing up to 45% TG.

EXAMPLE 4

The work then proceeded to in vivo experiments in a mouse model, which is accepted as a reliable system for predicting human efficacy.

Figure 7:
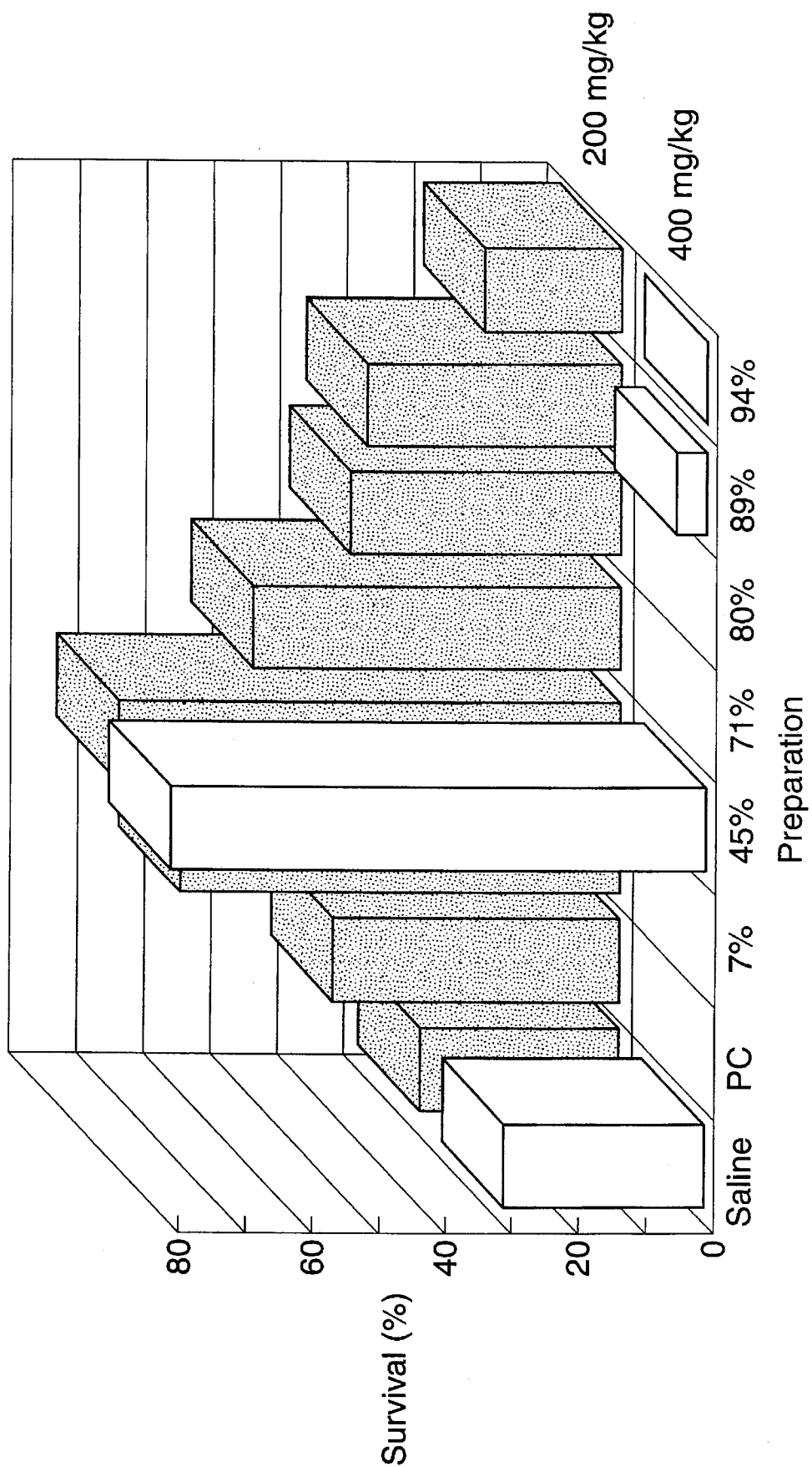
FIG. 7 presents reported information on toxicity associated with administration of various PC and PC/TG compositions in a mouse model, using a 70% toxicity model where E. coli LPS is administered.

In these experiments, mice were injected, in bolus form, with sufficient amounts of the formulations described in example 3 as well as others (pure phosphatidylcholine, 7% TG, 45% TG, 71% TG, 80% TG, 89% TG, 94% TG), or a saline control, to provide doses of phospholipid (either 200 mg/kg or 400 mg/kg), together with 25 mg/kg of E. coli 0111:B4 LPS. The control group received intravenous physiological saline in a volume sufficient to match the volume of emulsion. Survival after 72 hours is presented in FIG. 7.

Overall survival in the control group was 29%±8% (mean: 63 animals in 8 experiments). Each preparation was tested in a minimum of 3 experiments on 18 or more animals.

PC alone had a modest protective effect, not statistically significant at the 95% confidence level, while 7%, 45% and 71% TG compositions significantly improved survival. The 80% and 89% TG compositions were marginally effective, while the 94% TG decreased survival.

When the dose was increased to provide 400 mg/kg of PC both the 89% and 94% TG emulsions significantly decreased survival time, probably due to TG poisoning, as explained infra.

EXAMPLE 5

The work described in examples 2–4 established that phospholipids are an active agent useful in inhibiting endotoxemia. The fact that non-polar lipids other than triglycerides may form emulsions with phospholipids other than PC suggested that others may be tried. Exemplary are sphingomyelin (another phospholipid), and unesterified cholesterol (a polar neutral lipid), and mixtures of these. So, too, esterified cholesterol (a nonpolar ester), squalene (a hydrocarbon), and vitamin E (a nonpolar antioxidant) may be used. A series of experiments were designed to test these, using the human whole blood assay of example 2, supra, and the mouse survival assay of example 4.

Emulsions were prepared, in the manner described supra, using pure phosphatidylcholine, phosphatidylcholine with 10% (wt/wt) unesterified cholesterol, 10% (wt/wt) sphingomyelin, or 10% total of a mix of both. Emulsions were added to whole blood, at a concentration of 100 mg/dl, with reference to PC, and 10 ng/ml of LPS. The mixture was incubated, and TNF-α release measured.

Figure 8:
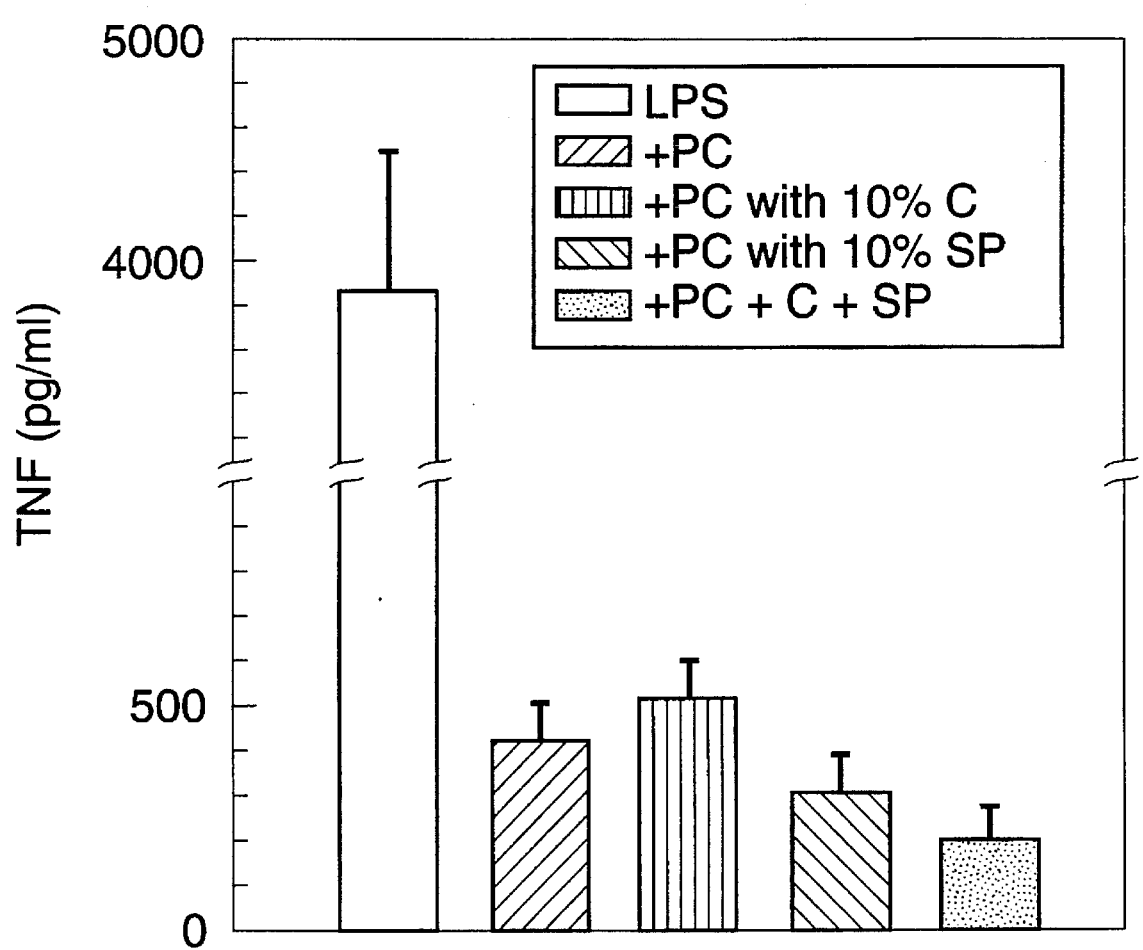
FIG. 8 shows data comparable to that secured for the human whole blood assay, supra, but using phospholipid with unesterified cholesterol, sphingomyelin, or mixtures of both, in place of triglycerides.

The results are shown in FIG. 8. TNF-α production was substantially reduced with PC alone. Emulsions containing unesterified cholesterol, sphingomyelin, or the mix of both, were also suppressive of TNF-α release.

EXAMPLE 6

The whole blood assay was also used to determine the effect of unesterified cholesterol and/or sphingomyelin to neutral lipid containing emulsions. Again, the emulsions were added at 100 mg/dl PC. The various compositions (wt/wt) are set forth in the following table.

| Emulsion | Composition |
| --- | --- |
| PC with 45% TG | 55:45 |
| PC + TG + C | 54.4:45.3:0.3 |
| PC + TG + SP | 51.6:43.0:5.4 |
| PC + TG + C + SP | 51.4:42.9:0.3:5.4 |
| PC + CE | 54.5:45.5 |
| PC + CE + C | 54.4:45.3:0.3 |
| PC + CE + SP | 51.6:43.0:5.4 |
| PC + CE + C + SP | 51.5:42.9:0.3:5.4 |

Figure 9A:
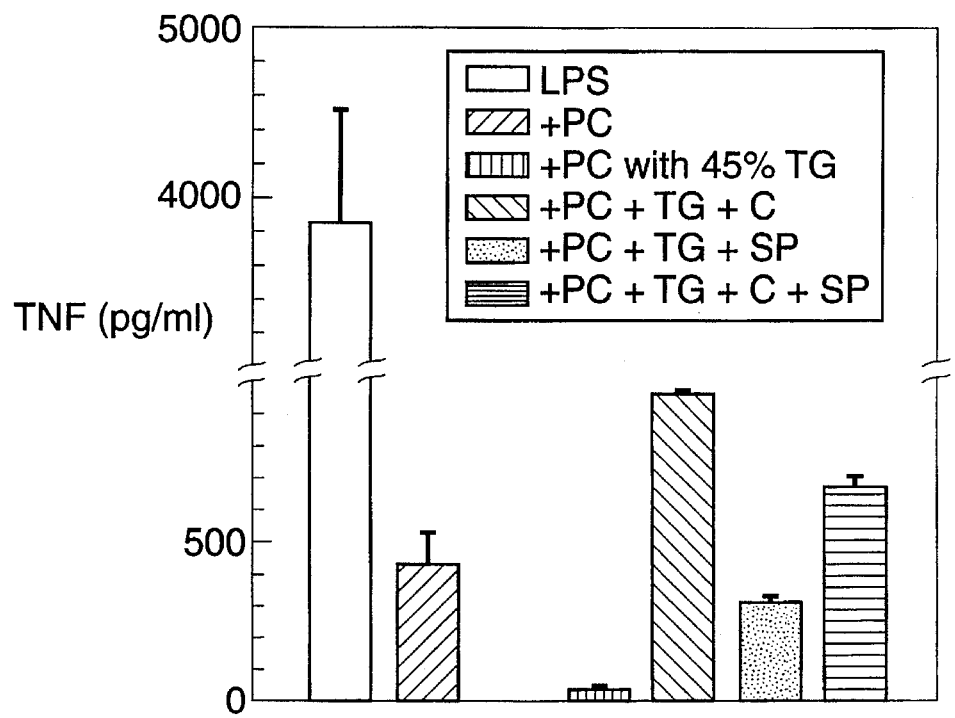
FIGS. 9A and 9B show results comparable to those shown in FIGS. 5A and 5B, except that in these new figures, phospholipid, unesterified cholesterol and/or sphingomyelin are mixed with triglycerides or esterified cholesterol as the neutral lipid.
Figure 9B:
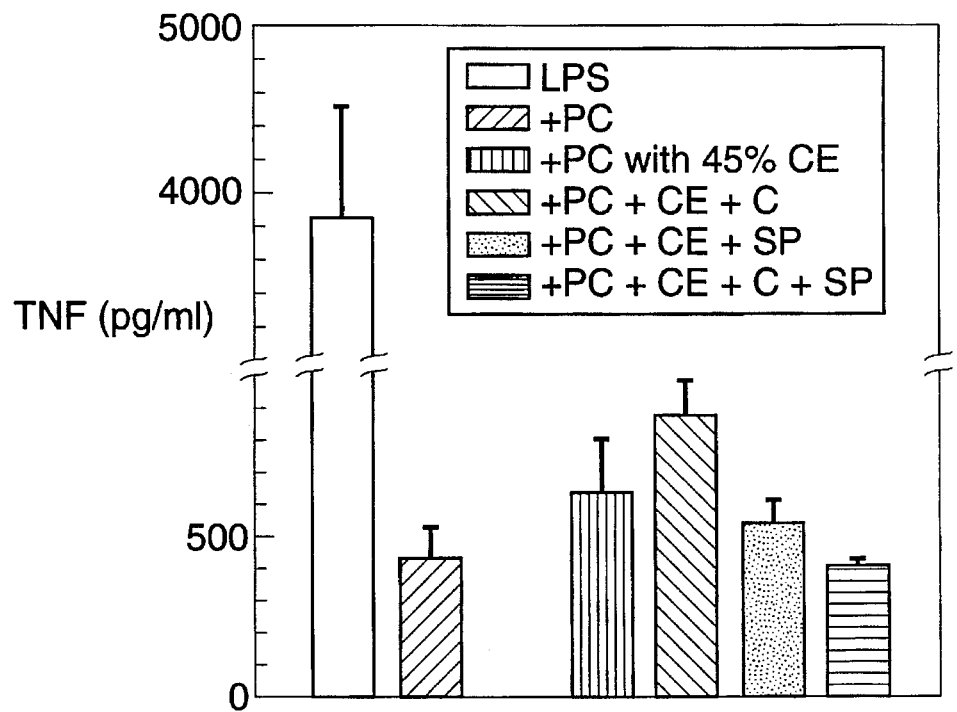
Figure 10:
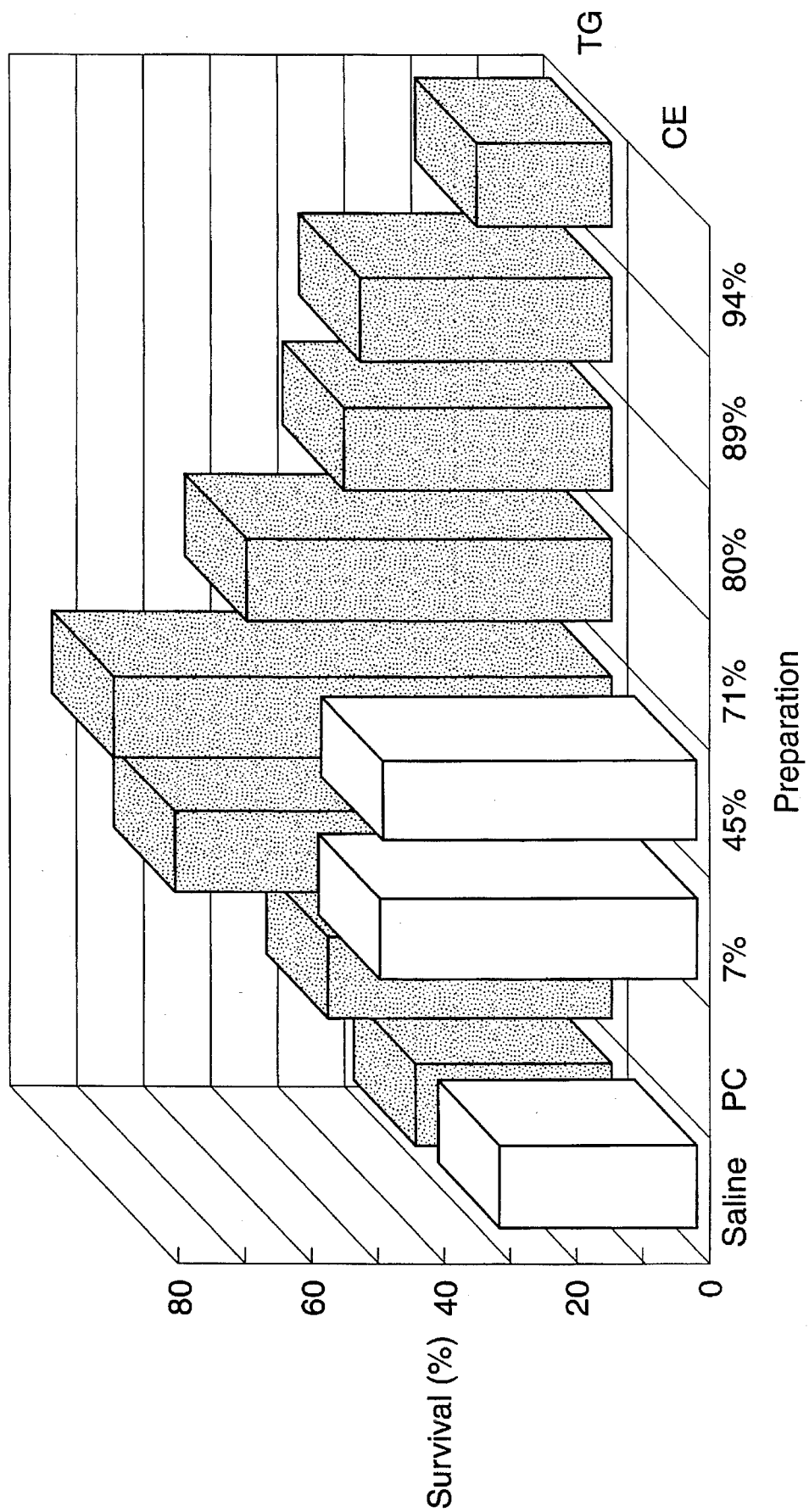
FIG. 10 compares results obtained from cholesterol ester and triglyceride containing emulsions, in the in vivo mouse model.
Figure 11:
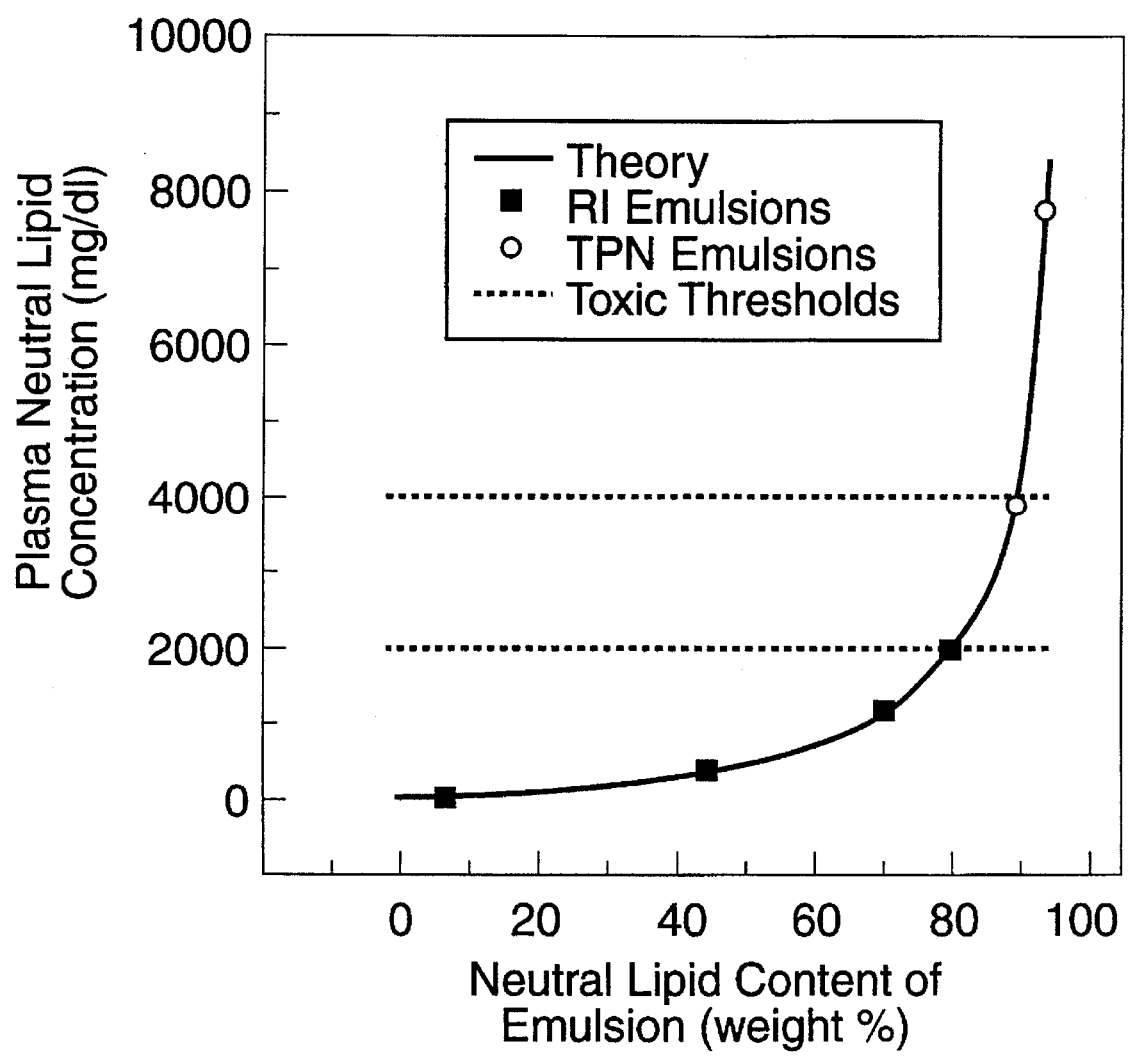
FIG. 11 graphs the theoretical amounts of triglycerides released into the blood following administration of various TG containing compositions, with toxicity thresholds. "TPN" stands for "total parenteral nutrition" while "RI" stands for compositions in accordance with the invention.

FIGS. 9A and 9B display the results. PC emulsions made with either neutral lipid, with or without additional polar lipids, demonstrated inhibition. Again, the LPS concentration used is a 70% lethal dose. The cholesterol ester containing emulsions are less effective than are TG containing emulsions, while those emulsions containing unesterified cholesterol did not suppress TNF-α as well as those emulsions which did not contain it. Adding sphingomyelin to the emulsions appeared to improve suppression of TNF-α production.

EXAMPLE 7

Cholesterol ester containing emulsions were tested in an in vivo model (i.e., that used in example 4), with a lethal dose of endotoxin. Emulsions were prepared with PC and TG, or PC and cholesterol ester (CE), and were administered to provide a single bolus dose of 200 mg/kg of PC, together with 25 mg/kg of *E. coli* 0111:B4 LPS (a lethal dose), through the tail vein. Control groups received intravenous physiological saline in a volume to match the volume of emulsion.

In FIG. 10, the data compare the results from the CE and TG containing emulsions. Each emulsion was tested in a minimum of two experiments, using a total of 16 or more animals.

As shown, emulsions containing 7% or 45% CE (wt %) significantly improved survival. These results, taken with those of example 6, show that CE can be substituted for TG to create emulsions that neutralize endotoxin.

EXAMPLE 8

Protein-free emulsions of phospholipid with triglyceride effectively block TNF-α production in whole blood stimulated with LPS. In theory, these emulsions might also be effective in vivo if they can be administered safely in doses that provide protective concentrations of phospholipid in plasma. Our previous experiments with R-HDL suggest that the minimum effective dose of phospholipid is approximately 200 mg/kg. Using this dose and a plasma volume of 4.5% of body weight, one can calculate the concentration of triglyceride expected in plasma following administration of a series of emulsions with increasing triglyceride content. The result is shown in FIG. 11 as a smooth line curving upward with increasing weight percent TG. Plasma TG concentrations rarely rise above 1000 mg/dl in healthy adults even after a fatty meal. Pancreatitis is reported in patients with plasma TG above 2000 mg/dl (Farmer, et al., Amer. J. Med. 54: 161–164 (1973); Krauss, et al., Amer. J. Med. 62: 144–149 (1977); Glueck, et al., J. Lab. Clin. Med. 123: 59–61). Plasma TG above 4000 mg/dl is extremely rare and cause for serious concern. The last two thresholds are shown by horizontal lines in the figure above. Administration of either 10% or 20% INTRALIPID® in a dose to provide 200 mg/kg phospholipid is expected to raise plasma TG concentrations (see the two open circles) well above the safe limits. By contrast, administration of emulsions containing 7%, 45%, 71% or 78% (solid squares left to right) raises plasma TG to 136, 477, 1300 or 2000 mg/dl respectively. Emulsions with TG content up to ~50% are expected to be free of toxicity from TG.

The foregoing examples detail the invention which involves, in one aspect, the alleviation or prevention of endotoxemia in a subject via administering an effective amount of a phospholipid with which an endotoxin associates. The association of phospholipid and endotoxin is then removed from the subject via standard biological processes well known to anyone familiar with processes via which lipoprotein particles are removed. Association of the endotoxin with the phospholipid inactivates it.

The subject being treated is preferably a human, but the practice of the invention is equally applicable in a veterinary context as well.

"Alleviation" as used herein refers to treatment to ease the burden of endotoxemia caused by any of the various endotoxins produced by, e.g., gram negative bacteria (*S. tymphimurium, E. coli,* etc.). Prophylaxis may be accomplished by administering the agent at a point where the subject is in or about to be in, a situation where endotoxin exposure may result. Classically, this occurs during surgery. Thus, a subject who is about to experience a surgical procedure may have the active ingredient administered preparatory to the procedure.

The effective amount of phospholipid necessary for treatment of the subject can vary. In general, a dose up to about 200 mg of phospholipid per kilogram of body weight of the subject is preferred, although the amount may drop, or increase, depending upon the severity of the endotoxemia or the degree of risk in the context of the prophylaxis.

It is desirable to administer the phospholipids in compositions which also contain neutral lipids, but this is not necessary, as neutral lipid free emulsions of phospholipids are also envisioned. The desirability of the administration with phospholipids results from the fact that the neutral lipids and phospholipids associate into particles which resemble the lipoproteins, but differ therefrom in that they contain no protein of peptide components, which are of course, always present in the lipoproteins.

Especially desirable forms of treatment are those where the phospholipid is a phosphatidylcholine, such as egg yolk phosphatidylcholine, soy based phosphatidylcholine or a sphingolipid. With respect to the neutral lipids, it is preferred to use cholesterol ester or triglyceride, but other neutral lipids, such as squalene or other hydrocarbon oils, di- and mono-glycerides and antioxidants such as vitamin E may also be used.

The form in which the compositions may be administered can vary, with a bolus or other intravenous forms being especially preferred. When a bolus form is used, and the composition contains triglyceride, e.g., some care must be given in dosing. It is fairly well known that triglycerides are toxic if administered in too large an amount. The artisan of ordinary skill, however, can easily formulate the compositions so that the risk of triglyceride poisoning is reduced, or eliminated. In general, when a bolus form is used, the compositions should contain no more than about 80 weight percent of triglyceride or other neutral lipid, preferably no more than 70 weight percent. Most preferably, the compositions should contain no more than about 50 weight percent, of neutral lipid, when a bolus is administered.

When non-bolus forms are employed, however, such as other intravenous forms, the risk of poisoning is decreased. Nonetheless, the ranges delineated supra are preferred for intravenous, or other forms of administration, although it must be understood that they are not required. Preferably, a dose of up to about 200 mg per kg of body weight of phospholipid is administered. Administration of up to about or even up to about 800 mg/kg is also feasible. Doses are general, however, and will vary depending upon the subject and the form of administration.

As indicated, supra, the protein and peptide free formulations require that at least one phospholipid be present. Preferably at least one neutral lipid is present optionally, these may include additional materials such as sterols (e.g., cholesterol, β-sitosterol), esterified or unesterified lipids (e.g., cholesterol ester or unesterified cholesterol), hydrocarbon oils such as squalene, antioxidants such as vitamin E, but these are not required. Of course, more than one phospholipid, and/or more than one neutral lipid may be used in any formulation.

Other aspects of the invention will be clear to the skilled artisan, and need not be repeated here.

It will be understood that the specification and examples are illustrative but not limitative of the present invention and that other embodiments within the spirit and scope of the invention will suggest themselves to those skilled in the art.

We claim:

1. Protein and peptide free composition useful in treating endotoxemia, comprising:
   (a) at least one neutral lipid at an amount equal to about 7% by weight total lipid in said composition, and
   (b) at least one phospholipid.

2. The protein and peptide free composition of claim 1, wherein said phospholipid is phosphatidyl-choline.

3. The protein and peptide free composition of claim 1, wherein said at least one neutral lipid comprises cholesteryl ester.

4. The protein and peptide free composition of claim 1, further comprising sphingosine.

5. The protein and peptide free composition of claim 1, wherein said at least one neutral lipid comprises a triglyceride.

6. Protein and peptide free composition useful in treating endotoxemia, comprising:
   (a) from about 7% to about 50% by weight of total lipid in said composition, of triglyceride, and
   (b) at least one phospholipid.

7. The protein and peptide free composition of claim 6, wherein said phospholipid is phosphatidyl-choline.

8. The protein and peptide free composition of claim 6, further comprising cholesteryl ester.

9. The protein and peptide free composition of claim 6, further comprising sphingosine.

* * * * *

(12) EX PARTE REEXAMINATION CERTIFICATE (5864th)
United States Patent
Parker et al.

(10) Number: US 5,614,507 C1
(45) Certificate Issued: *Aug. 21, 2007

(54) PROTEIN AND PEPTIDE FREE, NEUTRAL LIPID AND PHOSPHOLIPID CONTAINING COMPOSITIONS USEFUL IN TREATING ENDOTOXEMIA

(75) Inventors: Thomas S. Parker, Brooklyn, NY (US); Daniel M. Levine, New York, NY (US); Albert L. Rubin, Englewood, NJ (US); Bruce R. Gordon, New York, NY (US); Stuart D. Saal, New York, NY (US)

(73) Assignee: Sepsicure, L.L.C., Secaucus, NJ (US)

Reexamination Request:
No. 90/007,556, May 20, 2005

Reexamination Certificate for:
Patent No.: 5,614,507
Issued: Mar. 25, 1997
Appl. No.: 08/432,691
Filed: May 2, 1995

(*) Notice: This patent is subject to a terminal disclaimer.

Related U.S. Application Data

(60) Division of application No. 08/288,568, filed on Aug. 10, 1994, now Pat. No. 5,506,218, which is a continuation-in-part of application No. PCT/US93/07453, filed on Aug. 9, 1993, which is a continuation-in-part of application No. 07/928,930, filed on Aug. 12, 1992, now Pat. No. 5,344,822.

(51) Int. Cl.
*C07K 14/435* (2006.01)
*C07K 14/775* (2006.01)
*A61K 9/127* (2006.01)
*A61K 38/00* (2006.01)

(52) U.S. Cl. .................... 514/78; 514/182; 514/547

(58) Field of Classification Search ............ None
See application file for complete search history.

(56) References Cited

U.S. PATENT DOCUMENTS

| 4,115,313 | A | | 9/1978 | Lyon et al. |
|---|---|---|---|---|
| 4,314,997 | A | | 2/1982 | Shanbrom |
| 5,000,958 | A | | 3/1991 | Fountain et al. |
| 5,128,318 | A | | 7/1992 | Levine et al. |
| 5,578,583 | A | * | 11/1996 | Maranh ao ......... 514/49 |
| 5,652,339 | A | | 7/1997 | Lerch et al. |

FOREIGN PATENT DOCUMENTS

| DE | 25 56 592 A | 6/1977 |
|---|---|---|
| DE | 40 17 979 A1 | 12/1991 |
| DE | 43 10 935 A | 11/1993 |
| EP | 0 074 251 A | 3/1983 |
| EP | 0 391 369 A | 10/1990 |
| JP | 61 093 111 | 5/1986 |
| WO | WO-93/05797 | 4/1993 |

OTHER PUBLICATIONS

Kocsar, et al., "Effect of Bile Acids on the Intestinal Absorption of Endotoxins in Rats," J. BACT., 100:1, 220–223 (1969).

Schwarzenberg, et al., "Ursodeoxycholic Acid Modifies Gut–Derived Endotoxemia in Neonatal Rats," Ped. Res., 35:2, 214–217 (1994).

Anantharamaiah, "Synthetic Peptide Analogs of Apolipoproteins," Meth. In Enzymology, 128:627–647 (1986).

* cited by examiner

Primary Examiner—Evelyn Mei Huang

(57) ABSTRACT

Protein and peptide free compositions are described, which are useful in treating endotoxemia. The compositions contain a phospholipid and a neutral lipid, preferably phosphatidylcholine and triglyceride.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3 and 5–9 are cancelled.

Claim 4 is determined to be patentable as amended.

New claims 10 and 11 are added and determined to be patentable.

4. [The] *A* protein and peptide-free composition [of claim 1, further comprising] *useful in treating endotoxemia, comprising:*

(a) at least one neutral lipid in an amount equal to about 7% by weight total lipid in said composition (b) at least one phospholipid, and (c) sphingosine.

10. *A protein and peptide free composition useful in treating endotoxemia, comprising:*

*(a) about 7% by weight of total lipid in said composition, of triglyceride,*

*(b) phosphatidylcholine, in an amount of at least 55% by weight of the total lipid in said composition, and*

*(c) sphingosine.*

*11. The protein and peptide free composition of claim 10, further comprising cholesteryl ester.*

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO: 1:

Asp Trp Leu Lys Ala Phe Tyr Asp Lys Val Ala Glu Lys Leu Lys
                  5                        10                      15
Glu Ala Phe ( 2 ) INFORMATION FOR SEQ ID NO: 2:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO: 2:

Lys Trp Leu Asp Ala Phe Tyr Lys Asp Val Ala Lys Glu Leu Glu
                  5                        10                      15
Lys Ala Phe ( 2 ) INFORMATION FOR SEQ ID NO: 3:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO: 3:

Asp Trp Leu Lys Ala Phe Tyr Asp Lys Ala Glu Lys Leu Lys Glu
                  5                   10                  15
Ala Phe ( 2 ) INFORMATION FOR SEQ ID NO: 4:

( i ) SEQUENCE CHARACTERISTICS:
          ( A ) LENGTH: 22 amino acids
          ( B ) TYPE: amino acid
          ( D ) TOPOLOGY: linear ( x i ) SEQUENCE DESCRIPTION: SEQ ID NO: 4:

Pro Lys Leu Glu Glu Leu Lys Glu Lys Leu Lys Glu Leu Leu Glu
                  5                   10                  15
Lys Leu Lys Glu Lys Leu Ala
                  20

( 2 ) INFORMATION FOR SEQ ID NO: 5:

( i ) SEQUENCE CHARACTERISTICS:
          ( A ) LENGTH: 16 amino acids
          ( B ) TYPE: amino acid
          ( D ) TOPOLOGY: linear ( x i ) SEQUENCE DESCRIPTION: SEQ ID NO: 5:

Val Ser Ser Leu Lys Glu Tyr Trp Ser Ser Leu Lys Glu Ser Phe
                  5                   10                  15
Ser ( 2 ) INFORMATION FOR SEQ ID NO: 6:

( i ) SEQUENCE CHARACTERISTICS:
          ( A ) LENGTH: 20 amino acids
          ( B ) TYPE: amino acid
          ( D ) TOPOLOGY: linear ( x i ) SEQUENCE DESCRIPTION: SEQ ID NO: 6:

Val Ser Ser Leu Leu Ser Ser Leu Lys Glu Tyr Trp Ser Ser Leu
                  5                   10                  15
Lys Glu Ser Leu Ser
                  20

( 2 ) INFORMATION FOR SEQ ID NO: 7:

( i ) SEQUENCE CHARACTERISTICS:
          ( A ) LENGTH: 24 amino acids
          ( B ) TYPE: amino acid
          ( D ) TOPOLOGY: linear ( x i ) SEQUENCE DESCRIPTION: SEQ ID NO: 7:

Val Ser Ser Leu Leu Ser Ser Leu Leu Ser Ser Leu Lys Glu Tyr
                  5                   10                  15
Trp Ser Ser Leu Lys Glu Ser Glu Ser
                  20

( 2 ) INFORMATION FOR SEQ ID NO: 8:

( i ) SEQUENCE CHARACTERISTICS:
          ( A ) LENGTH: 22 amino acids
          ( B ) TYPE: amino acid
          ( D ) TOPOLOGY: linear ( x i ) SEQUENCE DESCRIPTION: SEQ ID NO: 8:

```
Pro  Val  Leu  Asp  Glu  Phe  Arg  Glu  Lys  Leu  Asn  Glu  Glu  Leu  Glu
                5                        10                          15
Ala  Leu  Lys  Gln  Lys  Met  Lys
                20
```

( 2 ) INFORMATION FOR SEQ ID NO: 9:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO: 9:

```
Pro  Leu  Ala  Glu  Asp  Leu  Gln  Thr  Lys  Leu  Asn  Glu  Asn  Val  Glu
                5                        10                          15
Asp  Leu  Arg  Lys  Gln  Leu  Val
                20
```